(12) United States Patent
Sanchez et al.

(10) Patent No.: US 12,422,426 B2
(45) Date of Patent: Sep. 23, 2025

(54) ELECTRICALLY INSULATED BLOCK-ON-ROTATING-RING TEST UNIT AND METHOD

(71) Applicant: Southwest Research Institute, San Antonio, TX (US)

(72) Inventors: Carlos J. Sanchez, San Antonio, TX (US); Peter Mark Lee, Fair Oaks Ranch, TX (US)

(73) Assignee: SOUTHWEST RESEARCH INSTITUTE, San Antonio, TX (US)

(*) Notice: Subject to any disclaimer, the term of this patent is extended or adjusted under 35 U.S.C. 154(b) by 188 days.

(21) Appl. No.: 18/472,599

(22) Filed: Sep. 22, 2023

(65) Prior Publication Data

US 2024/0102985 A1 Mar. 28, 2024

Related U.S. Application Data

(60) Provisional application No. 63/376,782, filed on Sep. 23, 2022.

(51) Int. Cl.
*G01N 33/28* (2006.01)
*B32B 1/08* (2006.01)
*B32B 27/00* (2006.01)
*G01N 27/00* (2006.01)
*G01N 27/02* (2006.01)

(52) U.S. Cl.
CPC ......... *G01N 33/2888* (2013.01); *G01N 27/00* (2013.01); *G01N 27/028* (2013.01); *B32B 1/08* (2013.01); *B32B 27/00* (2013.01); *B32B 2597/00* (2013.01)

(58) Field of Classification Search
CPC .. G01N 33/2888; G01N 27/028; G01N 27/00; B32B 1/08; B32B 2597/00; B32B 27/00
USPC ....................................................... 324/649
See application file for complete search history.

(56) References Cited

U.S. PATENT DOCUMENTS

| | | | |
|---|---|---|---|
| 2003/0141878 A1* | 7/2003 | Shinzou | G01R 31/60 324/539 |
| 2004/0046584 A1* | 3/2004 | Ollila | G01R 31/2862 324/750.08 |
| 2011/0220415 A1 | 9/2011 | Jin et al. | |
| 2013/0098144 A1 | 4/2013 | Oh et al. | |
| 2014/0178637 A1 | 6/2014 | Rajagopalan et al. | |

OTHER PUBLICATIONS

International Search Report and Written Opinion from related PCT application No. PCT/US2023/074851, dated Mar. 18, 2024.
Kawada, et al., "Friction Control by Applying Electric Potential under Lubrication with Ionic Liquids", Japanese Society of Tribologists (http://www.tribology.jp/), Tribology Online, vol. 14, No. 2 (2019), pp. 71-77, Tokyo, Japan.

(Continued)

*Primary Examiner* — Raul J Rios Russo
(74) *Attorney, Agent, or Firm* — Grossman, Tucker, Perreault & Pfleger, PLLC

(57) ABSTRACT

An electrically insulated block-on-rotating-ring test unit and method, to evaluate the effects of electrical potential on material pairs and fluids under mechanical load and in sliding contact. The fluids may comprise lubricants and oils utilized in electrical vehicles.

20 Claims, 4 Drawing Sheets

(56) References Cited

OTHER PUBLICATIONS

Spikes, "Triboelectrochemistry: Influence of Applied Electrical Potentials on Friction and Wear of Lubricated Contacts", Tribology Letters (2022) vol. 68, No. 90, pp. 1-27, London, United Kingdom.
Xie, et al., "Destabilization of lubrication oil micropool under charged conditions", Industrial Lubrication and Tribology, vol. 69, No. 1, 2017, pp. 59-64, Beijing, China.

* cited by examiner

ELECTRICALLY INSULATED BLOCK-ON-ROTATING-RING TEST UNIT AND METHOD

CROSS-REFERENCE TO RELATED APPLICATIONS

The present application claims priority to U.S. Provisional Application Ser. No. 63/376,782 filed Sep. 23, 2022 which is incorporated by reference.

FIELD

The present invention is directed at an electrically insulated block-on-rotating-ring test unit and method, to evaluate the effects of electrical potential on material pairs and lubricants under mechanical load and in sliding contact.

BACKGROUND

The influence of applied electrical potential on rubbing contacts, a topic sometimes identified as "tribo-electrochemistry" has assumed new attention with the development of hybrid-electric and electric vehicles. Namely, an evaluation of lubricant performance on the components of electric-motor and gear box performance in light of exposure to electrical potentials. This is particularly of growing importance in light of the observation that the impact of an applied electrical potential on friction and wear, in a lubricated system, may be beneficial or harmful, depending upon the nature of the applied potential and the characteristics of the frictionally engaged surfaces, as well as the selected lubricants employed for sliding type contact.

SUMMARY

An electrically insulated block-on-rotating ring test unit comprising an electrically isolated rotating ring, an electrically isolated block configured to be mechanically loaded against the electrically isolated rotating ring, a negative electrode in electrical communication with the block and a positive electrode in electrical communication with the ring, or vice-versa, wherein the negative and positive electrodes are configured to supply an electrical potential between the electrically isolated rotating ring and the electrically isolated block.

A method for evaluating the effects of electrical potential on one or more fluids in a test unit comprising supplying a test unit having an electrically isolated rotating ring, an electrically isolated block configured to be mechanically loaded against the electrically isolated rotating ring, a negative electrode in electrical communication with the block and a positive electrode in electrical communication with the ring, or vice-versa, wherein the negative and positive electrodes are configured to supply an electrical potential between the electrically isolated rotating ring and the electrically isolated block. This is followed by introducing one or more fluids between the electrically isolated rotating ring and the electrically isolated block. One may then rotate the ring relative to said block and apply a mechanical load and electrical potential between the electrically isolated block and the electrically isolated ring.

BRIEF DESCRIPTION OF THE DRAWINGS

The electrically insulated block and rotating-ring testing device is further described herein with reference to the accompanying drawings identified below.

DETAILED DESCRIPTION

Figure 1:
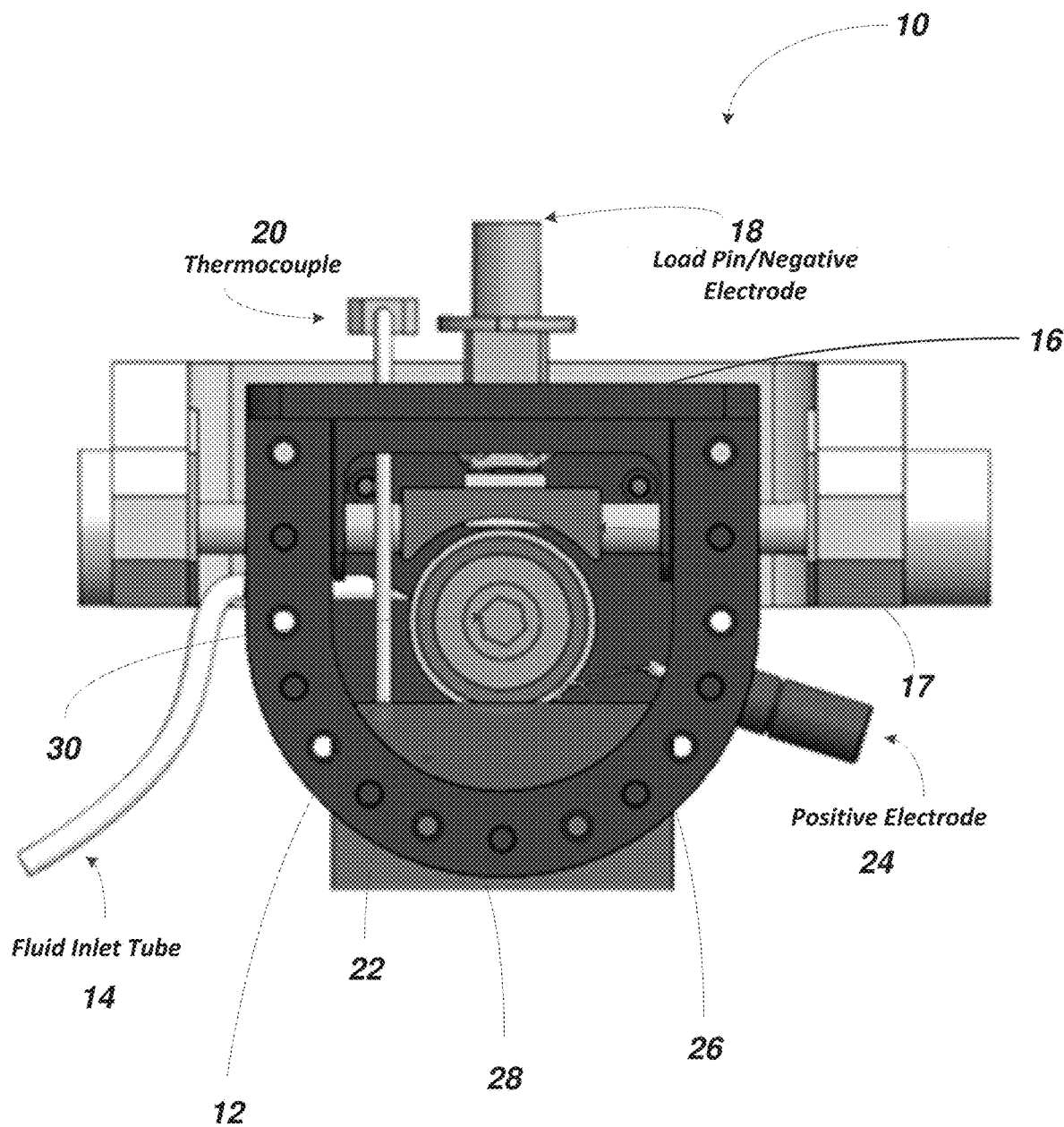
FIG. 1 provides a cross-sectional view of a preferred electrically insulated block and rotating-ring testing device.

The present invention is directed at a test unit and method to investigate the effects of electrical potential on material pairs or surfaces in sliding contact and the fluids, such as lubricants or oils used therein. A cross-sectional view of a contemplated and preferred electrically insulated block and rotating-ring testing device 10 is illustrated in FIG. 1.

As illustrated, there is an electrically isolated metallic or electrically conductive rotating ring 12 and a fluid inlet tube 14, to conveniently introduce one or a plurality of fluids that can optionally be externally heated. Such fluids may preferably be heated in the range of 20° C. to 225° C. Reference to electrically isolated means that the rotating ring is not in electrical communication with any other components of the testing device 10.

The fluid, such as an oil or lubricant so introduced, may then be configured to form a lubricant or oil pool 22 within the test device for continuously coating the rotating ring 12. A metallic or electrically conductive block 16, that is similarly electrically isolated from all other components of the testing device, is in communication with a load pin negative electrode 18 which is configured to apply both a mechanical load on block 16 with respect to rotating ring 12 and to accommodate introduction of a voltage potential to the block.

Also illustrated is thermocouple 20 that extends into the accumulation of lubricating oil 22 that is in contact with the rotating ring 12. The thermocouple therefore can provide a measurement of temperature of the fluid, namely oil or lubricant 22. A positive electrode is illustrated at 24 that preferably relies upon a coiled metallic or electrically conducting wire 26 that remains in contact with the metallic or electrically conducting rotating ring 12. The coiled electrically conducting wire is therefore preferably under spring tension and remains in electrical engagement to the rotating ring 12 as the ring rotates. Preferably, the coiled electrically conducting wire is made from phosphor bronze type wire, which are composed of copper-tin-phosphor alloy.

A housing is shown generally at 28 that is electrically isolated from the rotating ring 12 and block 16. Preferably, the housing may be made from an electrically insulating polymeric material. Preferably, all components of the test rig 10 are electrically isolated, so that an electrical potential, either AC or DC to be applied across block 16 and rotating ring 12 is without electrical interference. Accordingly, as shown, the block holder 17 and ring holder 30 are electrically insulated and preferably made from electrically insulating polymeric material. Moreover, the testing device 10 preferably includes a rotational seal that prevents the oil or lubricant 22 from interacting with the shaft bearings employed to rotate the ring 12.

As may also be appreciated, preferably, the fluid is temperature controlled via a resistive heater, remote from the test device 10, that is then pumped into the fluid inlet tube 14. This allows for the fluid, such as an oil or lubricant, to be heated without electrical interference to the test device 10.

Figure 2:
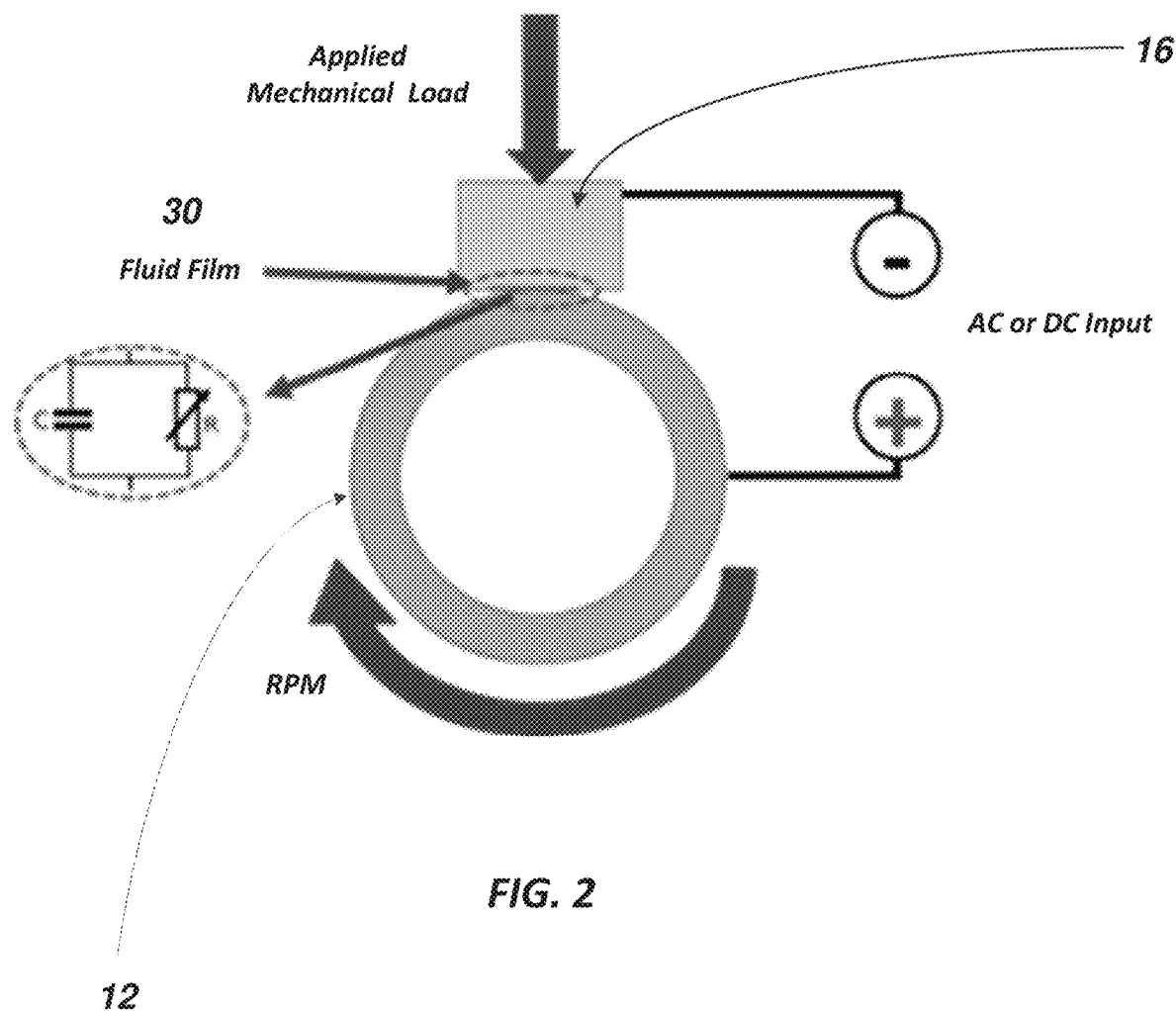
FIG. 2 provides an additional cross-sectional view of a preferred electrically insulated block and rotating-ring testing device.

An additional cross-sectional view of the test device 10 is shown in FIG. 2. Again, it is observed that the block 16 is configured so that it can be mechanically loaded against the rotating ring 12. The block preferably is engaged to a negative electrode and the ring is preferably engaged to a positive electrode, or the block is preferably engaged to the positive electrode and the negative electrode is engaged to the ring. An AC or DC potential may then be applied. For a given oil or lubricant, a fluid film 30 may then form between the sliding surfaces of the block 16 and ring 12 and create a resistive and capacitive circuit, depending upon the oil or lubricant properties and the testing conditions (electrical potential applied, speed, load and lubricant temperature).

In method form, the present invention relates to a method to evaluate the effects of electrical potential on sliding material pairs and the fluids, such as oils or lubricants used therein. The method includes providing the test device 10 including a fluid between the surfaces of the electrically isolated block 16 and electrically isolated ring 12. The ring 12 is then rotated at a selected rpm, a selected mechanical load is applied between the electrically isolated block and the electrically isolated ring, and an electrical potential, either AC or DC, is also applied between the electrically isolated block 16 and electrically isolated ring 12.

Among the metric outputs that are contemplated herein for evaluation by the test device 10, such may include an evaluation of the electrical properties of the fluids, such as oils or lubricants under an applied mechanical loading condition. That may include, but not be limited to an evaluation of the response of any selected oil or lubricant under a given electrical potential or varying electrical potential, to the shearing forces on the oil or lubricant provided the applied mechanical load on the block 16 relative to the rotating ring 12. By way of example, one may evaluate whether or not the applied electrical potential has any influence on the chemical composition, the oil or lubricant, and its ensuing lubricating properties, under a selected mechanical load condition.

Accordingly, one may evaluate herein the influence of lubricant or oil shearing, in the presence of an applied electrical potential, on the lubricating properties of a selected oil or lubricant, between a given material surface of block 16 and given material surface for ring 12. It is further contemplated that one may also monitor the dynamic coefficient of friction versus potential as between the rotating ring 12 and block 16, for a selected lubricant or oil. It is additionally contemplated that one may now also evaluate the impact of oil or lubricant aging, for a given applied potential, under selected shearing (ring rpm) conditions for a given applied load on block 16 over a selected period of time. One may also evaluate differences in wear rates. The lubricant or oil may be any fluid that is utilized in a vehicle that may provide lubrication and in particular lubrication for a given vehicular engine component.

Working Example

The test device herein was utilized to evaluate a variety of testing metric as summarized below in Table 1. The lubricants evaluated were an automatic transmission fluid 1 (ATF1) which is MERCON® ULV, an automatic transmission fluid 2 (ATF2) which is DEXRON®-VI and an automatic gear oil (AGO) which is OMALA J2360.

TABLE 1

Test Metrics Applied To The Electrically Insulated Block-On-Rotating Ring Test Unit

| Test Metric | Levels | Values |
| --- | --- | --- |
| Fluid Temperature | 6 | 20, 40, 60, 80, 100 and 120° C. |
| Voltage Type | 3 | No Voltage, Alternating Current (AC) and Direct Current (DC) |
| AC Frequency | 2 | 1 kHz and 20 kHz |
| AC Waveform | 2 | Sine and Square |
| Test Profile | 2 | Variable Load and Variable Speed |
| Lubricant | 3 | ATF 1, ATF2, AGO |

Figure 3:
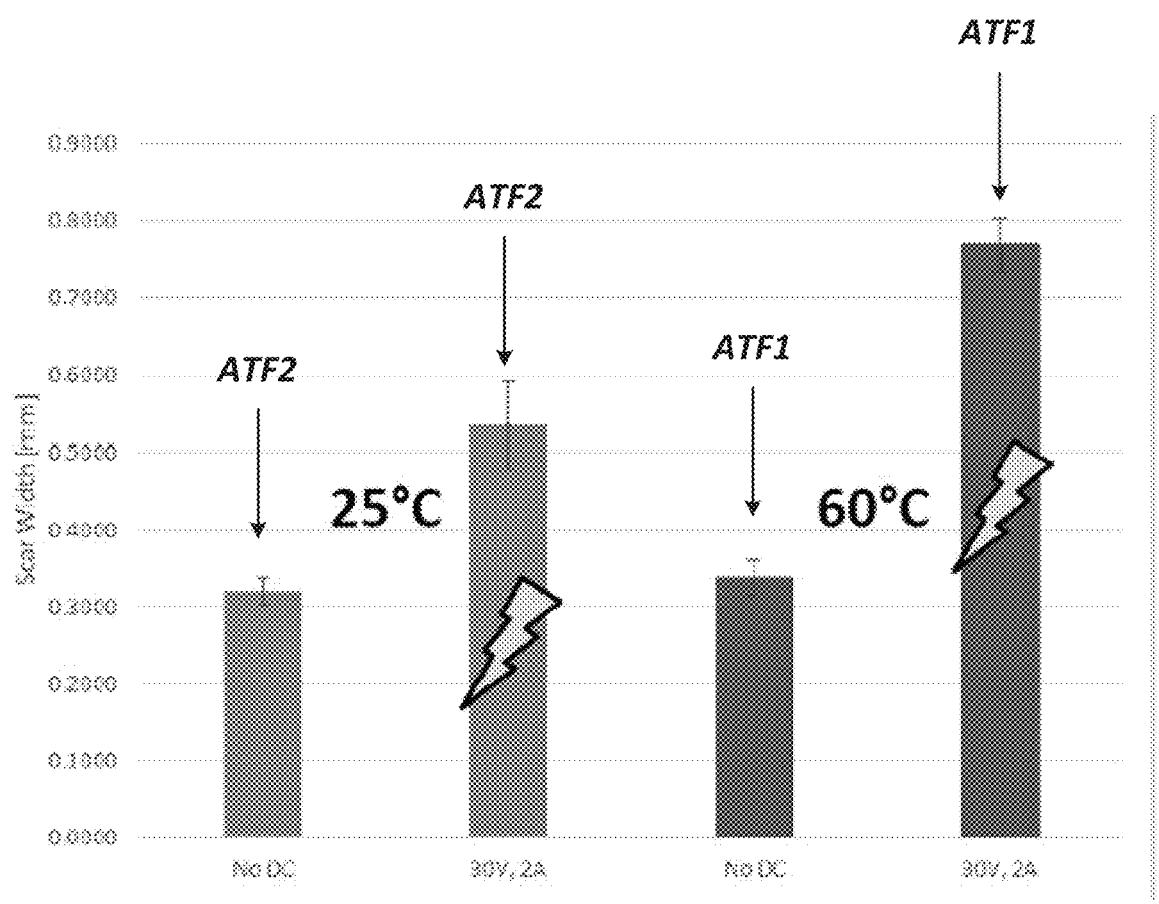
FIG. 3 is a plot of the block scar width at the indicated temperatures both with and without electrification as evaluated on the electrically insulated block and rotating-ring testing device.

The wear results for ATF1 and ATF2 are illustrated in FIG. 3, which plots what is identified as the block scar width at 25° C. and 60° C. respectively, without electrification (i.e. "No DC") and with application of a 30V, 2A DC input. Block scar width is a measurement of the width of the scar on the block 16 (FIG. 2) subsequent to testing. From FIG. 3 it can be seen that the width of the scar on the block increased for both ATF1 and ATF2 with the identified electrification. This confirms that electrification can effect the wear properties of a given lubricant.

Figure 4:
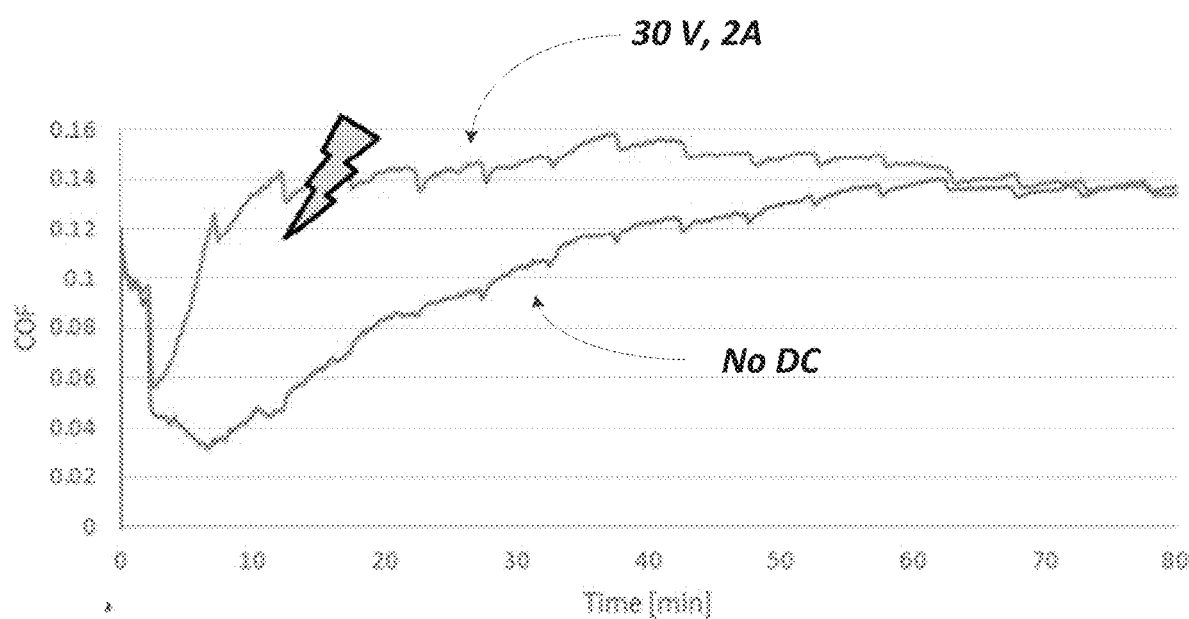
FIG. 4 is a plot of the effect of the coefficient of friction of ATF1 at 25° C. both without and with DC input as evaluated on the electrically insulated block and rotating-ring testing device.

FIG. 4 illustrates the effect of the coefficient of friction (COF) of ATF1 at 25° C. both without and with a DC input of 30V, 2A, for the same load conditions over time as evaluated in the electrically insulated block-on-rotating ring test unit. As can be seen, the coefficient of friction (COF) approached the same steady-state value of 0.14. However, this approach to steady-state was different depending upon the electrification. Namely, the steady state value of 0.14 was achieved relatively more quickly with the indicated electrification than without.

As those of skill in the art will appreciate, all of the above-mentioned contemplated test metrics of device 10 will be of importance and can now be evaluated as the electrical fluid properties of oil and lubricants become increasingly significant with the growth of electrification in power-providing engine designs and configurations.

The invention claimed is:

1. An electrically insulated block-on-rotating ring test unit comprising:
   an electrically isolated rotating ring;
   an electrically isolated block configured to be mechanically loaded against said electrically isolated rotating ring;
   a negative electrode in electrical communication with said electrically isolated block and a positive electrode in electrical communication with said electrically isolated rotating ring or a positive electrode in electrical communication with said electrically isolated block and a negative electrode in communication with said electrically isolated rotating ring, wherein said negative and positive electrodes are configured to supply an electrical potential between said electrically isolated rotating ring and said electrically isolated block.

2. The electrically insulated block-on-rotating ring test unit of claim 1 wherein said electrically isolated block and said electrically isolated rotating ring are composed of electrically insulated polymeric material.

3. The electrically insulated block-on-rotating ring test unit of claim 1 wherein said positive electrode or negative electrode, when in communication with said electrically isolated rotating ring, includes a spring tension to provide electrical engagement of said positive or negative electrode with said electrically isolated rotating ring.

4. The electrically insulated block-on-rotating ring test unit of claim 1 wherein said positive or negative electrode is composed of copper-tin-phosphor alloy.

5. The electrically insulated block-on-rotating ring test unit of claim 1 further including a fluid inlet configured to introduce a fluid into said test device for engagement with said electrically isolated rotating ring.

6. The electrically insulated block-on-rotating ring test unit of claim 5 further including a thermocouple configured to measure fluid temperature.

7. An electrically insulated block-on-rotating ring test unit comprising:
an electrically isolated rotating ring;
an electrically isolated block configured to be mechanically loaded against said electrically isolated rotating ring wherein said electrically isolated block and said electrically isolated rotating ring are composed of electrically insulated polymeric material;
a negative electrode in electrical communication with said electrically isolated block and a positive electrode in electrical communication with said electrically isolated rotating ring or a positive electrode in electrical communication with said electrically isolated block and a negative electrode in communication with said electrically isolated rotating ring, wherein said positive electrode or negative electrode, when in communication with said electrically isolated rotating ring, includes a spring tension to provide electrical engagement of said positive or negative electrode with said electrically isolated rotating ring; and
wherein said negative and positive electrodes are configured to supply an electrical potential between said electrically isolated rotating ring and said electrically isolated block.

8. The electrically insulated block-on-rotating ring test unit of claim 7 wherein said positive or negative electrode is composed of copper-tin-phosphor alloy.

9. The electrically insulated block-on-rotating ring test unit of claim 7 further including a fluid inlet configured to introduce a fluid into said test device for engagement with said electrically isolated rotating ring.

10. The electrically insulated block-on-rotating ring test unit of claim 7 further including a thermocouple configured to measure fluid temperature.

11. The method of claim 7 wherein said electrically isolated block and said electrically isolated rotating ring are composed of electrically insulated polymeric material.

12. The method of claim 7 wherein said positive or negative electrode, when in electrical communication with said electrically isolated rotating ring, includes a spring tension to provide electrical engagement of said positive or negative electrode with said electrically isolated rotating ring.

13. The method of claim 7 wherein said positive or negative electrode is composed of copper-tin-phosphor alloy.

14. The method of claim 7 further including a fluid inlet configured to introduce a fluid into said test device for engagement with said electrically isolated rotating ring.

15. The method of claim 14 further including a thermocouple configured to measure fluid temperature.

16. A method for evaluating the effects of electrical potential on one or more fluids in a test unit comprising:
supplying a test unit having an electrically isolated rotating ring, an electrically isolated block configured to be mechanically loaded against said electrically isolated rotating ring, a negative electrode in electrical communication with said electrically isolated block and a positive electrode in electrical communication with said electrically isolated rotating ring or a positive electrode in electrical communication with said electrically isolated block and a negative electrode in communication with said electrically isolated rotating ring, wherein said negative and positive electrodes are configured to supply an electrical potential between said electrically isolated rotating ring and said electrically isolated block;
introducing one or more fluids between said electrically isolated rotating ring and said electrically isolated block;
rotating said electrically isolated rotating ring relative to said electrically isolated block; and
applying a mechanical load and an electrical potential between said electrically isolated block and said electrically isolated rotating ring.

17. The method of claim 16 wherein the electrical potential an alternating current potential.

18. The method of claim 16 wherein the electrical potential applied is a direct current potential.

19. The method of claim 17 wherein the fluids are at a temperature in the range of 20° C. to 225° C.

20. The method of claim 17 wherein said fluid comprises a lubricant or an oil.

* * * * *